United States Patent
Johnson (10) Patent No.: US 9,345,561 B2
(45) Date of Patent: May 24, 2016

(54) FIREABLE DENTAL BLANK ASSEMBLY

(75) Inventor: Ryan E. Johnson, Peoria, IL (US)

(73) Assignee: 3M Innovative Properties Company, St. Paul, MN (US)

( * ) Notice: Subject to any disclaimer, the term of this patent is extended or adjusted under 35 U.S.C. 154(b) by 368 days.

(21) Appl. No.: 13/995,535

(22) PCT Filed: Dec. 20, 2011

(86) PCT No.: PCT/US2011/065959
§ 371 (c)(1),
(2), (4) Date: Jun. 19, 2013

(87) PCT Pub. No.: WO2012/087997
PCT Pub. Date: Jun. 28, 2012

(65) Prior Publication Data
US 2013/0288026 A1    Oct. 31, 2013

Related U.S. Application Data (60) Provisional application No. 61/425,798, filed on Dec. 22, 2010.

(51) Int. Cl.
*A61C 13/00* (2006.01)
*B32B 7/02* (2006.01)

(52) U.S. Cl.
CPC ............. *A61C 13/00* (2013.01); *A61C 13/0022* (2013.01); *B32B 7/02* (2013.01); *A61C 13/0004* (2013.01); *Y10T 428/24942* (2015.01)

(58) Field of Classification Search
CPC .............. A61C 13/00; A61C 13/0022; A61C 13/0004; A61C 13/0003; Y10T 428/24942; Y10T 428/12326; B32B 18/00; A61K 6/0205
See application file for complete search history.

(56) References Cited

U.S. PATENT DOCUMENTS 5,622,551 A     4/1997  Erbe
6,482,284 B1 *  11/2002 Reidt et al. ............... 156/200
(Continued)

FOREIGN PATENT DOCUMENTS

EP      2184030       5/2010
WO      WO 01/35854   5/2001
(Continued)

OTHER PUBLICATIONS

International Search Report PCT/US2011/065959 Apr. 20, 2012, 3 pgs.
(Continued)

*Primary Examiner* — Aaron Austin
*Assistant Examiner* — Jasper Saberi
(74) *Attorney, Agent, or Firm* — Nicole J. Einerson (57) ABSTRACT

A fineable dental blank assembly. The assembly can include a blank and a support coupled to the blank to facilitate machining of the blank. The blank can be adapted to be machined to form at least a portion of dental appliance, and can be formed of at least one of a glass, a glass-ceramic, a porcelain, and a ceramic. The support can be formed of at least one of a high melting point metal (or metal alloy) and a ceramic, wherein the blank and the support are separately formed. The assembly can further include a bonding composition positioned between the blank and the support. Other means for coupling the blank and the support can include a direct bond and/or mechanical inter-engagement. The assembly can be configured to withstand temperatures necessary to fire at least a portion of the assembly in a downstream firing process.

19 Claims, 2 Drawing Sheets

(56) References Cited

U.S. PATENT DOCUMENTS

| | | | |
|---|---|---|---|
| 6,527,550 B1 * | 3/2003 | Hajjar et al. | 433/53 |
| 6,669,875 B2 | 12/2003 | Meyertholen | |
| 7,605,817 B2 | 10/2009 | Zhang | |
| 7,698,014 B2 | 4/2010 | Dunne | |
| 2004/0155975 A1 | 8/2004 | Hart | |
| 2005/0276672 A1 | 12/2005 | Prince | |
| 2010/0058588 A1 | 3/2010 | Heinz | |
| 2012/0193823 A1 * | 8/2012 | Goetzinger et al. | 264/16 |
| 2012/0251979 A1 * | 10/2012 | Karim | A61C 8/005 433/201.1 |

FOREIGN PATENT DOCUMENTS

| | | |
|---|---|---|
| WO | WO 2009/070469 | 6/2009 |
| WO | WO 2011/106132 | 9/2011 |
| WO | WO 2011/159503 | 12/2011 |
| WO | WO 2011/159520 | 12/2011 |
| WO | WO 2012/087999 | 6/2012 |

OTHER PUBLICATIONS

Beuer et al., "High-strength CAD/CAM-fabricated veneering material sintered to zirconia copings-A new fabrication mode for all-ceramic restorations", Dental Materials 25 (2009) 121-128.

"Porcelain Veneer Materials", About Porcelain Veneers© 2101—[online-printed Nov. 8, 02010], 3 pages. <www.aboutporcelainveneers.com/index.cfm/PV-Materials.cfm>.

"Glass Ceramic Block for Cerec® and inLab", Technical Product Profile—Paradigm C; 3M ESPE (03.06); 32 pgs.

\* cited by examiner

FIREABLE DENTAL BLANK ASSEMBLY

FIELD

The present disclosure generally relates to dental blank assemblies comprising a blank coupled to a support, the blank adapted to be formed into a dental appliance, and the support adapted to support the blank, for example, during a machining process and/or during handling. The present disclosure particularly relates to dental blank assemblies that can be fired, and more particularly, relates to fireable dental blank assemblies adapted for use with digital dentistry workflows.

BACKGROUND

Dental supports (e.g., mandrels) can be used to support a dental blank during machining and/or handling. For example, some dental supports can be designed to fit within specific mills that can be used in chairside and/or laboratory processes, such as those that employ computer controlled machining equipment (e.g., a CAD/CAM device). Some existing dental supports, or dental blank assemblies comprising supports, that can be employed in such dental machining processes, are formed of inexpensive alloy metals that can be precisely cast or machined to a specific shape, but which would not withstand the high temperatures necessary to fire, glaze or crystallize the dental appliance. As such, no intermediate heating steps can be employed in forming the desired dental appliance while the blank is still attached to the support.

SUMMARY

The fireable dental blank assembly of the present disclosure comprises a support that is configured to withstand any temperature that could be seen during the processing of the blank (i.e., a "fireable support"). Such fireable dental blank assemblies can be particularly useful in forming all-ceramic dental appliances, and, in some embodiments, the fireable dental blank assemblies of the present disclosure themselves can be all-ceramic. Furthermore, the dental blank assemblies of the present disclosure can be used to make multilayer, all-ceramic dental appliances, because multiple ceramic layers can be formed, including any necessary firing steps, while the blank remains coupled to the support. Particularly, the fireable dental blank assemblies of the present disclosure can be used to form anatomical and/or multichromatic dental appliances, such as dental restorations (e.g., crowns, bridges, etc.). An "anatomical" crown, for example, can not only be formed of more than one material and layer, but can also include specific mammelon structure (and/or shading) that mimics the anatomical structure of a natural tooth. In addition, "multichromatic" dental appliances, for example, can include shading to mimic an enamel layer in a first, outer layer and shading to mimic a dentin layer in a second, inner layer.

On the contrary, existing blank assemblies that do not employ a fireable support, could not create an anatomical, all-ceramic dental appliance because any intermediate heating (e.g., firing) step would melt or soften the support. Such melting or softening of the support could lead to the destruction of the support; the support and blank losing their known relative dimensions or positions; and/or the support no longer fitting properly in the machining equipment. In addition, or alternatively, such heating steps can melt or soften the bonding composition coupling the blank and the support, or otherwise destroy the connection between the blank and the support (e.g., such that the blank is no longer properly secured to the support for further machining and/or handling). As a result, any such intermediate heating steps of non-fireable blank assemblies would ultimately render the blank assembly inoperable for any additional processing.

Some embodiments of the present disclosure provide a fireable dental blank assembly. The assembly can include a blank adapted to be machined to form at least a portion of dental appliance, and can be formed of at least one of a glass, a glass-ceramic, a porcelain, and a ceramic. The assembly can further include a support coupled to the blank to facilitate downstream machining processes of the blank. The support can be formed of at least one of a high melting point metal (or metal alloy) and a ceramic, wherein the blank and the support are separately formed. The assembly can further include a bonding composition positioned between the blank and the support to couple the blank and the support, the bonding composition having a bonding temperature that is lower than a softening temperature of the blank and that is lower than a softening temperature of the support. A high melting point metal can be a metal or metal alloy that has a melting point that is higher than a firing temperature of the blank, and that is higher than the bonding temperature of the bonding composition. The blank can have a first coefficient of thermal expansion (CTE), the support can have a second CTE, and the bonding composition can have a third CTE. The first CTE and the second CTE can differ by no more than 2.0, the second CTE and the third CTE can differ by no more than 2.0, and the first CTE and the third CTE can differ by no more than 2.0. The assembly can be configured to withstand temperatures necessary to fire at least a portion of the assembly in a downstream firing process.

Some embodiments of the present disclosure provide a fireable dental blank assembly. The assembly can include a blank adapted to be machined to form a dental appliance, and can be formed of at least one of a glass, a glass-ceramic, a porcelain, and a ceramic. The assembly can further include a support coupled to the blank to facilitate downstream machining processes. The support can be formed of at least one of a high melting point metal (or metal alloy) and a ceramic, wherein the blank and the support are separately formed. The assembly can further include means for coupling the blank and the support, wherein the means for coupling is adapted to withstand temperatures necessary to fire at least a portion of the assembly. A high melting point metal is a metal or metal alloy that has a melting point that is higher than a firing temperature of the blank. Each component of the assembly can have a coefficient of thermal expansion (CTE) that differs from a CTE of other components of the assembly by no more than 2.0. The assembly can be configured to withstand temperatures necessary to fire at least a portion of the assembly in a downstream firing process.

Other features and aspects of the present disclosure will become apparent by consideration of the detailed description and accompanying drawings.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," "supported," and "coupled" and variations thereof are used broadly and encompass both direct and indirect connections, supports, and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a dental blank assembly (sometimes referred to as a "blank assembly" or a "mill blank assembly") that can be fired, and that can be used in a variety of digital dentistry workflows. The dental blank assembly of the present disclosure can include a support and a blank (e.g., a mill blank) coupled to the support. The support can be used to provide support, proper positioning and/or registration of the blank for machining (e.g., in a dental mill) or handling. A dental appliance (e.g., a dental restoration) can be formed from the blank. In some embodiments, the dental blank assembly of the present disclosure makes possible multi-step processing of a dental appliance (e.g., for making multilayer dental appliances), where the blank can remain coupled to the support until the dental appliance is completed. For example, in some embodiments, the blank can remain coupled to the support throughout any firing steps that may occur during the processing of the blank. That is, in some embodiments, the support can be configured to withstand firing temperatures used to fire (e.g., densify) the blank at various stages in making a dental appliance.

In multi-step processing of dental appliances, it can be important for the support to retain its shape and dimensions within precise tolerances so as to be precisely and repeatedly registered with respect to one or more tools or pieces of equipment (e.g., milling machines). In such multi-steps processes, for example, an outer layer of the dental appliance can be formed in one step, and an inner layer formed in a subsequent step, either in the same or a different tool (e.g., mill). The inner layer needs to be properly oriented and positioned with respect to the outer layer; thus, it can be important for the support to retain its shape and dimensions to allow proper repeated registration of the support in the tool.

As a result, the support of the present disclosure can be particularly suited for multi-step processing of an all-ceramic dental appliance. For example, in some embodiments, the dental blank assembly, and the support, can be used to form a desired outer shape in the blank (e.g., by milling), which can then be milled to have an inner cavity having the desired inner shape (e.g., mammelon structure), and which can then be filled with a second material, and a desired inner shape (e.g., to accommodate a tooth stump and/or implant abutment) can be formed (e.g., milled) in the second material. As a result, the entire outer and inner three-dimensional shape of the dental appliance need not be known prior to beginning the process, but rather the process can be separated into multiple steps, and such multiple steps can include a firing step, because the support can remain coupled to the blank in any of the above processing steps and can withstand any firing steps necessary to accomplish such processing. For example, in some embodiments, the blank can be fired, while still coupled to the support, after the desired outer shape is formed; in addition or alternatively, the outer layer having the desired cavity formed therein can be fired while still coupled to the support; and additionally or alternatively, the appliance can be fired, while still coupled to the support, after the second material is filled into the cavity, i.e., before or after the desired inner shape is formed therein. Examples of processes for making multilayer all-ceramic dental appliances are described in greater detail in U.S. Pat. No. 8,844,139, which is incorporated herein by reference in its entirety.

In addition, the dental blank assembly can include a means for coupling the blank and the support, and the means for coupling the blank and the support can also be configured to withstand the firing temperatures. Furthermore, the blank, the support, and the coupling means can each be configured to mechanically withstand downstream machining processes, such as milling, so that the dental blank assembly as a whole has the mechanical integrity necessary to withstand downstream machining process(es). In this way, the blank can remain securely and reliably coupled to the support throughout machining of the blank.

Examples of methods for making multilayer dental appliances that can be facilitated by the dental blank assembly of the present disclosure are described in U.S. Pat. No. 8,844,139.

The phrase "dental article" is to be understood as an article which can and is to be used in the dental or orthodontic area including dental laboratories, and can be used to describe even intermediates in a dental workflow process.

The phrase "dental appliance" generally refers to any dental or orthodontic appliance or restoration, dental mill blank, prosthetic device, or combination thereof. The appliance may be a finished appliance ready for introduction into the mouth of a patient, an appliance without the finishing (e.g. without stains) but with its final shape (i.e., a "net shape" appliance), or it may be a preformed or near-final dental appliance (i.e., a "near-net shape" appliance) subject to further processing before use, such as a dental mill blank.

The phrases "blank," "mill blank," "dental mill blank," "mill block," and "block" can be used interchangeably and generally refer to a solid block of material from which a desired product (e.g., a dental restoration) can be machined, and is not limited to the type of machining that will be used, even if referred to as a "mill" blank. A blank may have a size of about 10 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. In some embodiments, a blank used for making a single crown can have a diameter of about 24 mm and a length of about 19 mm. In some embodiments, a blank used for making bridges can have a diameter of about 24 mm and a length of about 58 mm. In general, blanks are attached to a support, stub, or mandrel that fits into a milling machine.

The terms "support," "support section," "stub," "mandrel," "milling support," and "milling mandrel" can be used interchangeably and generally refer to a structure that can provide support, positioning, mounting, and/or registration of the blank during machining (e.g., in a dental mill) or handling. Supports can include rod-shaped, cylindrical, or "hat"-shaped structures, but can also be understood to include other structures, such as frames (e.g., a LAVA™ frame available from 3M ESPE, Seefeld, Germany).

The term "machining" generally refers to shaping a material by a machine, and can be employed to create custom-fit dental appliances having a desired shape and morphology. Machining can include, but is not limited to, one or more of milling, grinding, cutting, carving, abrading, polishing, controlled vaporization, electric discharge milling (EDM), cutting by water jet or laser, any other suitable method of cutting, removing, shaping or carving material, or a combination thereof. In some cases, milling can be faster and more cost-effective than grinding. The terms "blank," "mill blank," "dental mill blank," "mill block," and "block" can be used to describe a starting material that will be machined to form a dental appliance.

While machining a blank using a hand-held tool or instrument is possible, machining of the present disclosure particularly refers to machining by subtractive CAD/CAM processes, in which a digital workflow is used to determine the desired shape or features (e.g., in three dimensions), and/or to guide the machining process to remove material in order to form the desired shape. By way of example, in some embodiments, a specially designed tooth-shape (e.g., a positive of the tooth-shape and/or a negative of the tooth-shape) can be produced by a digital workflow. Such a digital workflow can include scanning a patient's mouth to develop a model for the desired dental appliance. Such scanning can be performed using an optical scanner that is coupled to a computer-aided design (CAD) system that functions in conjunction with a computer-integrated manufacturing (CIM) or computer-aided manufacturing (CAM) system. Such a CAD/CAM system is available, for example, under the trade designation LAVA™ from 3M ESPE AG (Seefeld, Germany).

Some embodiments of the present disclosure employ a CAD/CAM device capable of milling a blank, such as the Cerec System (available from Sirona Dental Systems, Germany) By using a CAD/CAM machining (e.g., milling) device, the dental appliance can be fabricated efficiently and with precision. During machining, the contact area may be dry, or it may be flushed with a lubricant. Alternatively, it may be flushed with an air or gas stream. Suitable lubricants can include water, oil, glycerin, ethylene glycols, silicones, or combinations thereof. After machining, some degree of finishing, polishing and adjustment may be necessary to obtain a custom fit and/or aesthetic appearance.

The phrase "dental restoration" is generally used to refer to any restoration that can be used in the dental field, including, but not limited to, crowns, partial crowns, inlays, onlays, abutments, bridges (e.g., including 2-unit, 3-unit, 4-unit, 5-unit or 6-unit bridges), implants, other suitable dental articles, and combinations thereof. The dental restoration can include a three-dimensional inner and outer surface including convex and concave structures. The thickness of a dental restoration can vary from very thin, for example at its edges and rims (e.g., less than about 0.1 mm) to considerably thick, for example, in the biting, or occlusal, area (e.g., up to about 7 mm). In some embodiments, the thickness of a dental restoration ranges from 0.3 mm to 0.5 mm.

The terms "ceramic" or "all-ceramic" are generally used to refer to materials that are considered to fall within the broad material class of "ceramic," and are formed of glass, glass-ceramic, porcelain, ceramic, or combinations thereof. For example, a "ceramic" or "all-ceramic" blank, support, dental blank assembly, or dental appliance would not include any structures formed of organic polymeric materials.

The term "glass" generally refers to a hard, brittle, transparent solid. Examples of glasses can include, but are not limited to, silica, borosilicate glass, sodium oxide, potassium oxide, calcium oxide, flint glass, soda-lime glass, other suitable glass components, or combinations thereof. A glass can include an inorganic product of fusion that has been cooled to a rigid condition without crystallizing. Some glasses contain silica as their main component and a certain amount of glass former.

The phrase "glass ceramic" generally refers to a material sharing many properties with both glass and more crystalline ceramics. It is formed as a glass, and then made to crystallize partly by heat treatment. The space between the crystallites is filled by the glassy matrix. Glass ceramics mainly refer to a mixture of alkali metal-, silicon-, and aluminium-oxides.

The term "porcelain" generally refers to a clay-based ceramic. Clay products are generally classified into two subclasses—structural clay products and whitewares. Porcelain is an example of a whiteware in that porcelain becomes white and/or translucent after high-temperature firing. Porcelains are generally formed of clay (e.g., including alumina ($Al_2O_3$), silica ($SiO_2$), and other impurities) and other non-clay materials, such as flint, quartz, kaolin, and feldspar. Feldspars generally include aluminosilicate materials that contain $K^+$, $Na^+$, and $Ca^{2+}$ ions.

The term "ceramic" generally refers to an inorganic non-metallic material that can be produced by application of heat. Ceramics can be hard, porous and brittle and, in contrast to glasses or glass ceramics, can display an essentially purely crystalline structure.

The phrase "softening temperature" or "softening point" generally refers to the temperature, or range of temperatures, at which a material (e.g., in a solid phase) begins to slump under its own weight. For metals, in the present disclosure, the softening point is generally regarded as being the melting point of the metal or metal alloy. However, for materials that do not have a definite melting point, the softening point may be the temperature at which viscous flow of the material changes to plastic flow. For example, the softening point of a glass, a glass-ceramic, or a porcelain may occur at a glass-transition temperature of the material, and may be defined by a viscosity of 10 poise, in some embodiments, a viscosity of 10^4 poise, in some embodiments, a viscosity of 10^7.65 poise, and in some embodiments, a viscosity of 10^13 poise.

Any of the above materials—glasses, glass-ceramics, porcelains and ceramics—can shrink upon drying and/or firing, but a more detectable and/or significant amount of shrinkage may occur with ceramics, as compared to glasses, glass-ceramics, and porcelains.

The term "sintering" generally refers to making objects from a powder by heating the material (e.g., below its melting point—"solid state sintering") until its particles adhere to each other. Sintering can cause the densification of a porous material to a less porous material (or a material having less cells) having a higher density. In some cases, sintering can also include changes of the material phase composition (e.g., a partial conversion of an amorphous phase toward a crystalline phase).

The terms "sintering" and "firing" are used interchangeably herein. A pre-sintered ceramic framework can shrink during a sintering step, that is, if an adequate temperature is applied. The sintering temperature to be applied depends on the material chosen. For example, for $ZrO_2$-based ceramics, a sintering temperature (e.g., for sintering to full density) can range from about 1200° C. to about 1600° C. In some embodiments, $Al_2O_3$-based ceramics can be sintered at a temperature ranging from about 1300° C. to about 1700° C. However, if the dental blank assembly of the present disclosure will be fired as an assembly, the blank can be selected so as not to shrink to a point where it would detach from the support.

In some embodiments, in general, sintering of a glass and/or glass ceramic material to full density can be effected at a temperature of at least about 700° C., and in some embodiments, at least about 750° C. In some embodiments, sintering to full density of a glass and/or glass ceramic material can be effected at a temperature of no greater than about 1000° C., and in some embodiments, no greater than about 950° C. In some embodiments, sintering to full density of a glass and/or glass ceramic material can be effected in a temperature range of from about 700° C. to about 1000° C., and in some embodiments, from about 750° C. to about 950° C., for example, for a period of about 1 to about 3 hours.

As a result, in some embodiments, the dental blank assembly of the present disclosure, or a portion thereof, such as the support, may need to be able to withstand a firing temperature (e.g., of a downstream or intermediate firing step) of at least about 600° C. (e.g., according to the American Dental Association's definition of an "all-ceramic" dental restoration), in some embodiments, at least about 750° C., in some embodiments, at least about 800° C., in some embodiments, at least about 950° C., in some embodiments, at least about 1000° C., in some embodiments, at least about 1100° C., and in some embodiments, at least about 1200° C.

Figure 1:
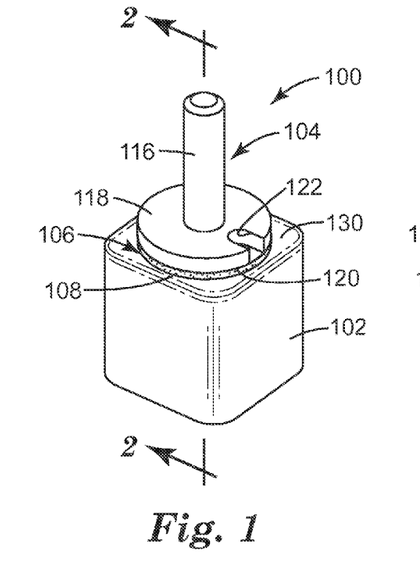
FIG. 1 is a perspective view of a dental blank assembly according to one embodiment of the present disclosure.
Figure 2:
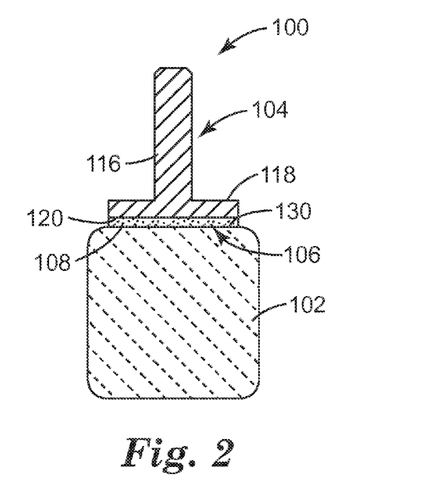
FIG. 2 is a cross-sectional side view of the dental blank assembly of FIG. 1, taken along line 2-2 of FIG. 1.

FIGS. 1-2 illustrate a dental blank assembly 100 according to one embodiment of the present disclosure. As shown in FIGS. 1-2, the dental blank assembly 100 can include a blank 102, a support 104 and a means 106 for coupling the blank 102 and the support 104. As shown in FIG. 2, in some embodiments, the means 106 for coupling the blank 102 and the support 104 can include a bonding composition 108. In some embodiments, the bonding composition 108 can be referred to as a "bonding layer" which can further be described as comprising, consisting of, or consisting essentially of the bonding composition 108. The bonding composition 108 is described in greater detail below.

The support 104 can be formed of at least one of a high melting point metal or metal alloy, and a ceramic. Generally, a "high melting point metal" is a metal, or metal alloy, that has a melting point that is higher than a firing temperature of the blank 102 (or any temperature at which the blank 102 will be fired during processing of the dental blank assembly 100 or formation of a dental appliance), and that is higher than the softening temperature of the bonding composition 108, or at least an initial softening temperature of the bonding composition 108, otherwise referred to as the "bonding temperature" of the bonding composition 108, i.e., the temperature at which the bonding composition 108 is used to bond the blank 102 and the support 104. Particularly, a high melting point metal is a metal that has a melting point that is higher than any processing temperature to which the dental blank assembly 100 will be exposed. In embodiments in which the other components (e.g., the blank 102 and the bonding composition 108, if employed) are generally low-melting point materials (e.g., glasses or glass-ceramics), the metal or metal alloy of the support 104 can have a melting point that is higher than softening temperatures of the other components of the dental blank assembly 100.

In some embodiments, a high melting point metal is a metal having a melting temperature (e.g., softening temperature) greater than about 600° C., in some embodiments, at greater than about 750° C., in some embodiments, greater than about 800° C., in some embodiments, greater than about 950° C., in some embodiments, greater than about 1000° C., in some embodiments, greater than about 1100° C., and in some embodiments, greater than about 1200° C.

Examples of metals or metal alloys that can be employed in the support 104 include, but are not limited to, cobalt chromium, nickel chromium, gold, silver palladium, titanium, other suitable metals or metal alloys, and combinations thereof. Metal alloys having high melting points are used in the dental industry for the fabrication of restorations and restoration components, e.g. porcelain fused to metal crowns. These alloys may be precious metal alloys, or they may be non-precious metal alloys, which are more economical for use as the support 104. Such alloys can be casted into desired support (e.g., mandrel) shapes using investment casting and casting furnaces. Many of the alloys exhibit excellent adhesion to ceramic materials. For the non-precious alloys, such as cobalt-chrome and nickel-chrome alloys, Coefficients of Thermal Expansions (CTEs) generally range from 14-16 ppm, and melting ranges are generally 1200-1420° C. Such alloys are available from multiple suppliers, for example, from Bego USA (Lincoln, R.I.) under the trade names Wirobond, Wirocer, Wiron. Other suppliers include Jensen Dental (New Haven, Conn.), and Ivoclar (Liechtenstein).

Examples of ceramics that can be employed in the support 104 include, but are not limited to, zirconia ($ZrO_2$), alumina ($Al_2O_3$), spinel ($MgAl_2O_4$), leucite (e.g., chemically-derived, such as that described in U.S. Pat. No. 5,622,551), and combinations thereof.

As shown in FIGS. 1 and 2, the support 104 can include a shaft 116 having a longitudinal axis. In the embodiment of FIGS. 1-2, the shaft 116 has an overall cylindrical shape, although other shapes are also possible. For example, the shaft 116 could have a hexagonal shape or an octagonal shape in reference planes perpendicular to its central, longitudinal axis. In general, the support 104 can be shaped and dimensioned to facilitate the dental blank assembly 100 being inserted and reliably held by machining equipment, such as a milling machine. For example, in some embodiments, as shown in FIGS. 1 and 2, an outer end of the shaft 116 can be chamfered to facilitate insertion of the dental blank assembly 100 into a collet or a chuck of machining equipment, such as a milling machine.

As shown, in some embodiments, the support 104 can also include a flange 118 that is connected to an end of the shaft 116 that is opposite the chamfered end. The flange 118 as shown in the drawings also has a cylindrical shape, but has a diameter somewhat larger than the diameter of the shaft 116. In some embodiments, as shown, the central axis of the flange 118 can be collinear with the central axis of the shaft 116, and can presents a flat, outwardly facing bonding surface 120.

However, the flange 118 may have shapes other than cylindrical. For example, the flange 118 may have an overall square, hexagonal or octagonal shape in reference planes perpendicular to its central axis. Moreover, the central axis of the flange 118 may be laterally offset from the central axis of the shaft 116, if desired.

In some embodiments, as shown in FIG. 1, the flange 118 can also includes a notch 122 for registering or indexing the dental blank assembly 100 with respect to machining equipment, for example, for receiving an indexing pin of a milling machine. As shown in the FIGS. 1 and 2, the notch 122 can extend along the outer cylindrical wall of the flange 118, and can extend inwardly toward the central axis of the flange 118. Optionally, but not necessarily, the notch 122 can have a curved inner wall such that the notch 122 presents an overall, generally "U"-shaped configuration when looking in a direction along the central axis of the shaft 116.

In some embodiments, the support 104 may also have other features that align or enhance the coupling between machining equipment and the dental blank assembly 100. For example, the shaft 116 may have a recess or a groove that extends about its circumference to receive a setscrew or other structure of a collet or chuck. Other types of alignment or coupling-enhancing features are also possible, depending on the type of machine(s) selected.

Optionally, all or a portion of the outer cylindrical wall of the flange 118 can provide a calibration surface for use during the machining process (e.g., milling) to establish tool wear. Although the calibration surface in this embodiment has the shape of a cylinder or partial cylinder, other shapes are also possible. The calibration surface may be located next to the notch 122 or alternatively may be located on the peripheral wall in an area opposite the notch 122 relative to the central axis of the flange 118.

If a calibration surface is employed, the calibration surface can be manufactured to be located a precise distance, within very precise dimensional tolerances, from the central axis of the flange 118. For example, in some embodiments, the dimensional tolerance can be plus or minus 0.1 mm, in some embodiments, plus or minus 0.05 mm, and in some embodiments, plus or minus 0.01 mm.

The calibration surface can be used by a machine (e.g., a mill), typically before the machining process begins, as a reference surface to accurately determine the overall dimension (such as the length) of the machining tool (e.g., milling too). As an example, the machine may rotate the tool while slowly moving the tool toward the calibration surface. The machine can have a speed sensor for detecting the rotational speed of the tool and a positional sensor for tracking the axial position of the tool. The rotational speed of the tool slightly decreases as soon as the tool contacts the calibration surface. The machine can be programmed to determine the overall length of the tool and compensate for tool wear by determining the axial position of the tool (i.e., the distance from the central axis of the flange 118) in relation to the calibration surface as soon as a decrease in the rotational speed is detected. Other methods to use the calibration surface as a reference surface are also possible, such as methods that employ laser sighting techniques.

The blank 102 can include any three-dimensional or cross-sectional shape desired, which can be determined at least partially by the type of machining to be performed on the blank 102, and/or the type of material forming the blank 102. By way of example only, the blank 102 of FIGS. 1 and 2 has a generally cuboid shape, with somewhat rounded corners; however, other shapes are possible, such as cylindrical, pyramidal, conical, frusto-pyramidal, frusto-conical, polyhedral, parallelipipedal, other suitable shapes, or combinations thereof.

In addition, in some embodiments, the blank 102 can have a shape in reference planes perpendicular to its central axis that is rectangular, square, hexagonal or other types of polygons or non-polygons including oval. In some embodiments, as shown in FIGS. 1 and 2, the central axis of the blank 102 can be collinear with the central axis of the support 104. By way of example only, the blank 102 of FIGS. 1 and 2 has cross-sectional dimension (e.g., a diameter, if circular in cross-section) that is larger than the cross-sectional dimension (e.g., diameter) of the flange 118 of the support 104, but in some embodiments, the blank 102 can have a cross-sectional dimension that is smaller than a cross-sectional dimension of the flange 118 of the support 104. See, for example, FIGS. 4 and 5, which are described below.

The blank 102 can be formed of a variety of materials that are generally classified as a "ceramic," including, but not limited to, one or more of glasses, glass-ceramics, porcelains, ceramics, and combinations thereof. In general, the blank 102 and the support 104 are separately formed (i.e., not formed of a unitary or integral construction), and in some embodiments, are formed of different materials.

In some embodiments, employing a support 104 and a blank 102 that are formed independently of one another (i.e., "separately formed") can provide the following advantages or benefits: (i) the support 104 can be dimensionally stable, irrespective of the blank 102 and further processing of the blank 102 that may be necessary, so that the support 104 can fit repeatedly and reliably into a machine (e.g., a dental mill); (ii) the blank 102 and the support 104 can be conveniently and separately prepared and later joined (or one of the blank 102 and the support 104 can be formed simultaneously with coupling the blank 102 and the support 104 together), such that the individual needs of each of the blank 102 and the support 104 can be met without consideration for the other until the blank 102 and the support 104 need to be joined together (e.g., the support 104 may need to be shaped within precise tolerances to repeatedly and reliably fit in a desired machine, and the blank 102 needs to be adapted for processing into a dental appliance); (iii) the support 104 can be detached, cleaned and reused after the blank 102 has been formed into the desired dental appliance; (iv) the support 104 can be formed of a less-expensive material than that of the blank 102 (e.g., glass and glass-ceramic materials may not make economically sensible choices for the support 104); and (v) some glasses and/or glass-ceramics that may make excellent blank materials may be too brittle to use as the support 104, because they may not be able to withstand the forces necessary to securely hold (e.g., by a screw) the support 104 in a machine (e.g., in a collet or chuck). The above potential benefits also apply when the blank 102 and the support 104 are formed of different materials.

Examples of glasses that can be employed in the blank 102 of the present disclosure include, but are not limited to, silica, borosilicate glass, sodium oxide, potassium oxide, calcium oxide, flint glass, soda-lime glass, other suitable glass components, or combinations thereof.

Examples of glass-ceramics that can be employed in the blank 102 of the present disclosure include, but are not limited to, lithium disilicate, leucite-reinforced glass-ceramics, and combinations thereof. Other examples of suitable glass-ceramic materials that can be employed include, but are not limited to, Vita Mark II (available from Vita Zahnfabrik, Germany or Vident, USA), Empress CAD (available from Ivoclar Vivadent, Lichtenstein), Paradigm C (available from 3M ESPE, Seefeld, Germany), E-Max CAD (Ivoclar Vivadent), other suitable glass-ceramic materials, or combinations thereof.

Examples of porcelains that can be employed in the blank 102 of the present disclosure include, but are not limited to, feldspathic porcelains.

Examples of ceramics that can be employed in the blank 102 of the present disclosure include, but are not limited to, zirconia ($ZrO_2$), alumina ($Al_2O_3$), spinel ($MgAl_2O_4$), leucite (e.g., chemically-derived, such as that described in U.S. Pat.

No. 5,622,551), and combinations thereof. In some embodiments, a fully sintered or fully densified ceramic can be employed such that the blank 102 does not undergo significant shrinkage during processing that may compromise the attachment of the blank 102 with the support 104 and/or the bonding composition 108.

The bonding composition 108 can be used to bond the blank 102 and the support 104 together, and can enhance the bond and connection between the blank 102 and the support 104. Specifically, the bonding composition 108 can be positioned to bond together the support bonding surface 120 and a bonding surface 130 of the blank 102. As shown in FIG. 2, in some embodiments, the bonding composition 108 can extend along entire interfacial area between the bonding surfaces 120 and 130. In other embodiments, the bonding composition 108 may not extend along the entire interfacial area between the bonding surfaces 120 and 130.

Using a bonding composition can be beneficial to increase the bonding strength between the respective surfaces of the blank 102 and the support 104. Without the bonding composition 108, in some embodiments, it might happen that the individual parts do not adhere sufficiently together. This, however, can also depend on the geometry of the parts to be adhered together.

Using a bonding composition can also be beneficial in that it helps improving the fit of the blank 102 and the support 104, e.g. by filling small cavities or recesses in the bonding surfaces 120 and 130. In addition, use of the bonding composition 108 can allow for more facile methods of making the dental blank assembly 100, for example, rather than requiring any specific molding steps to join the blank 102 directly to the support 104. An example of a dental blank assembly formed by directly bonding the blank and the support is described below with reference to FIG. 3.

In some embodiments, the bonding composition 108 which can be used for bonding the blank 102 and the support 104 includes water, a glass and/or glass ceramic material, and optionally a rheological modifier.

In some embodiments, the bonding composition 108 may comprise a rheological modifier. In such embodiments, the rheological modifier may have a molecular weight above about 500,000. The bonding composition 108 may also comprise polyethylene glycol, typically with a molecular weight below about 10,000.

According to one embodiment, the bonding composition 108 can be characterized by one or more of the following features:

Viscosity of liquid without glass and/or glass ceramic material: being in the range of about 10 mPas to about 1,000 mPas or being in the range of about 20 mPas to about 500 mPas, or being in the range of about 30 mPas to about 100 mPas measured at 23° C. with a shear rate of 50 s$^{-1}$ (measured with a viscosimeter MCR301 (Anton Paar Comp.), cone plate geometry, diameter 25 mm, temperature of 23° C., shear rates d(gamma)/dt of 50 s$^{-1}$).

Viscosity of the bonding composition 108 (including glass and/or glass ceramic material): being in the range of about 500 to about 20,000 mPas, or about 1000 to about 10,000 mPas or about 1500 to about 5000 mPas.

If desired, the viscosity measurement can be done a follows: A viscosimeter MCR301 (from Anton Paar Comp.) can be used. A portion of the liquid/powder composition is placed between two steel discs with a diameter of 8 mm and a gap of 1 mm at a temperature of 23° C. The gap is filled completely with the liquid/powder composition. Excess liquid/powder composition is removed. To avoid an undesired drying of the slurry during the measurement a ribbon of wetted paper tissue is laid around the discs in order to raise the humidity. The shear rate between the rotating discs d(gamma)/dt is set constantly to 50 s$^{-1}$. The measurement is done 500 s after starting the shearing process of the composition.

In some embodiments, the bonding composition 108 can be combusted without leaving organic residues, if heated up to a temperature of about 750° C. for about 1 min. at ambient pressure (e.g. 1013 mbar). That is, in some embodiments, the content of organic components (containing carbon) in the bonding composition 108 can be below about 7 wt.-%, in some embodiments, below about 3 wt.-%, and in some embodiments, below about 2 wt.-% with respect to the total weight of the bonding composition 108.

The term "can be combusted without leaving organic residues" means that if about 200 mg of the composition is heated up to a temperature of about 750° C. for about 1 min. at ambient pressure, no visible (visible with the human eye) deposits can be found. That is, the composition either evaporates or can be burnt producing only gaseous components including carbon oxide and water. Except for the glass and/or glass ceramic material being present in the composition essentially no further components are left. This can be determined, if desired, e.g. by visually (with the human eye only) inspecting a final dental restoration obtained after a firing step. A grayish appearance of the dental restoration can be an indicator for a dental composition not fulfilling the above mentioned feature. For example, using a glycerol containing composition typically leads to a dental restoration having a grayish appearance, something which is typically not desirable.

In some embodiments, a metal support can be cast and/or machined to a desired three-dimensional shape, or otherwise formed according to known metal processing methods. In some embodiments, an existing support (e.g., a mandrel for a dental milling machine) can be digitally scanned to obtain a digital surface representation of the desired three-dimensional shape. Then, that digital surface representation can be used to machine (e.g., using CAD/CAM software) the desired support shape out of a desired block of material (e.g., a ceramic dental mill blank, such as a LAVA™ zirconia mill blank, available from 3M ESPE, Seefeld, Germany), factoring in a shrinkage parameter if a ceramic (e.g., zirconia) is employed, such that the resulting support 104 is the proper size after sintering. If the support 104 is formed of a ceramic material, the machined support 104 can then be fully sintered according to the ceramic manufacturer's specifications to achieve a ceramic support that has been sintered to its final or full density. Such sintering can be done, for example, is a LAVA™ furnace available from 3M ESPE.

In embodiments employing a bonding composition 108, the blank 102 can be any commercially available blank that meets the specifications of the present disclosure (e.g., has the proper softening temperature and coefficient of thermal expansion (CTE) for use with the desired support and bonding composition 108, etc.). Otherwise, the blank 102 formed of the desired material can be formed to any desired shape (e.g., block-like, i.e., parallelipipedal) by conventional methods, such as molding, machining, casting, other suitable methods, or combinations thereof.

The blank 102 and the support 104, thus formed, can then be coupled together using the bonding composition 108. For example, the bonding composition 108 can be applied (e.g., coated, painted, brushed, or the like) onto the bonding surface 120 of the support 104 (or a portion thereof) and/or the bonding surface 130 of the blank 102 (or a portion thereof). In some embodiments, the bonding composition 108 can be liberally applied. The support 104 and the blank 102 can then be pressed together, for example, manually using finger pressure, or using a machine or clamp. The assembly can then be heated (e.g., fired) to set, fire, crystallize, or the like, the bonding composition 108. The heating regime can be according to the manufacturer's specifications of the bonding composition 108, and/or can generally include a temperature profile that begins at a temperature lower than the softening temperature of the bonding composition 108 and is gradually increased to a temperature above the softening temperature of the bonding composition 108. By way of example only, in some embodiments, the temperature profile can begin at a temperature of at least 400° C., can be ramped at 30-50° C./min. to a temperature of at least about 600° C., 850° C., 900° C., or another suitable temperature above the softening temperature of the bonding composition 108.

The resulting dental blank assembly 100 can then be cooled, thus producing the dental blank assembly 100 comprising the blank 102 and the support 104 coupled together with the bonding composition 108.

As described above, the components of the dental blank assemblies of the present disclosure need to be coupled together with sufficient structural integrity and dimensional stability that allows for downstream processing, such as machining (e.g., millng, grinding, etc.) and handling.

As further described above, the softening temperature or range of temperatures of the various components of the dental blank assemblies of the present disclosure need to relate to one another in a particular way to ensure operability and usability of the dental blank assembly 100 as intended (e.g., in downstream heating steps, including firing, glazing, etc.). In general, the softening temperature of the support 104 needs to be high enough to withstand any temperature to which the dental blank assembly 100 will be exposed, both in forming the dental blank assembly 100 (e.g., a bonding temperature necessary to bond the blank 102 and the support 104 with the bonding composition 108), and in any downstream heating steps, such as firing, glazing, fusing additional layers of the dental appliance to the blank 102, etc. For example, in some embodiments, the blank 102 can be milled to form an outer layer, the outer layer can be filled with an additional ceramic-based material (e.g., ceramic, glass, glass-ceramic, and/or porcelain), and the two layers can be fired to fuse or bond the two layers together, and to dry and/or at least partially crystallize one or more of the layers. In such embodiments, the support 104 would generally need to withstand the temperatures at which the additional layer of the dental appliance is formed. In addition, in such embodiments, the blank 102 may further crystallize or densify, but generally retains its shape, size and aspect ratio, such that the attachment of the blank 102 with the support 104 and/or the bonding composition 108.

That is, the support 104 should generally have a softening temperature that is high enough that the support 104 does not undergo an expansion or contraction of the bulk material which would cause unexpected stress to form at the interface between the support 104 and the bonding composition 108 and/or the interface between the support 104 and the blank 102. In addition, the softening temperature of the support 104 is generally high enough to avoid any irreversible changes to the support 104 during any processing steps, e.g., firing, that might affect the fit of the support 104 into a machine (e.g., a milling machine).

In addition, the softening temperature of the support 104 can be higher than the softening temperature of the blank 102, although, the softening temperature of the blank 102 also needs to be high enough to withstand any temperature to which the dental blank assembly 100 will be exposed, both in forming the dental blank assembly 100 (e.g., a bonding temperature necessary to bond the blank 102 and the support 104 with the bonding composition 108) and in any downstream heating steps. As a result, the softening temperature of the support 104 and the softening temperature of the blank 102 are generally higher than the softening temperature of the bonding composition 108 (e.g., the bonding temperature of the bonding composition 108), higher than the bonding temperature at which the bonding composition 108 is used to bond the blank 102 and the support 104, higher than any firing temperatures of the blank 102, higher than any glazing temperatures, and higher than any temperatures necessary to fire, fuse, dry and/or crystallize additional ceramic-based layers of a dental appliance formed on or in the blank 102.

In embodiments in which the bonding composition 108 is employed to couple the blank 102 and the support 104, the bonding temperature at which the blank 102 is coupled to the support 104 is generally higher than the softening temperature of the bonding composition 108 (or at least an initial softening temperature of the bonding composition 108), such that the bonding composition 108 is in its softened, molten or liquid state to bond the blank 102 and the support 104, and then is allowed to cool, dry and/or crystallize to bond the blank 102 and the support 104 together.

In some embodiments, the bonding composition 108 can change after various heating steps, such that the softening temperature of the bonding composition 108 can increase, at least with a first heating step. In such embodiments, the known softening temperature of a bonding composition 108 can be used to bond the blank 102 and the support 104, but the softening temperature of the bonding composition 108 may then increase as a result of such heating steps, similar to an annealing process. In such embodiments, subsequent firing and/or glazing temperatures of the blank 102 may actually occur at temperatures higher than the softening temperature used in the first softening step to bond the blank 102 and the support 104, without destruction (e.g., softening, deforming, etc.) of the bonding composition 108. Such an embodiment is exemplified in Working Examples 1 and 2.

Similarly, the crystalline structure of any of the materials used as the blank 102 or the support 104 can also change as a result of heating, such that the material properties (e.g., softening temperature) can change, depending on the heat history of the material. For example, a lithium silicate may be used as the blank 102 and can be machined when in a precursor state (e.g., lithium silicate, lithium metasilicate) and then fired to change or increase the crystalline structure (e.g., to become a lithium disilicate), and the resulting material may be harder, tougher, etc. than the precursor state, such that the resulting material is suitable as a dental appliance.

As a result, in some embodiments, the order of softening temperatures, from lowest to highest, can be as follows: (1) blank 102 firing and/or glazing, or firing or fusing of additional dental appliance layers; (2) bonding temperature used to originally soften the bonding composition 108 to couple the blank 102 and the support 104; (3) the softening temperature of the blank 102; and (4) the softening temperature of the support 104. As described above, the softening temperature of the bonding composition 108 can change as a response to being exposed to higher temperatures (e.g., after the first softening step used to bond the blank 102 and the support 104), but generally, at any given point in time, the softening temperature of the bonding composition 108 may be between (1) the temperatures at which the blank 102 or additional layers of the dental appliance are fired, fused or glazed, and (2) the softening temperatures of the blank 102 and the support 104 (e.g., such that the blank 102 and the support 104 can withstand the bonding process).

Table 1 lists several exemplary materials that can be employed in the dental blank assembly 100 of the present disclosure as either the blank 102, the support 104, or the bonding composition 108, if employed, along with some material properties for those materials.

TABLE 1

Material properties of various materials that can be employed in the dental blank assemblies of the present disclosure.

| Material | Softening temp (° C.) | CTE (ppm) | Flexural Strength (MPa) |
|---|---|---|---|
| Zirconia | 1500 | 10-10.8 | 900-1200 |
| Lithium disilicate (E MAX CAD[1]) | 850-900 | 10.5 | 360 |
| LAVA ™ ceram porcelain | 820 | 10 | 95 |
| Feldspathic ceramic (VITA VM9[2]) | 670 | 8.8-9.2 | 100 |
| Feldspathic porcelain (VITA Mk II[3]) | 780 | 9.4 | 113 |
| Alumina | 1750 | 8.2 | 379 |
| Leucite reinforced ceramic[4] | Varies[5] | | |
| Non-precious metal dental alloys | Ranges from 1200-1420 | Ranges from 14-16 | |
| Glass solder | Various | | |

[1]available from Ivoclar Vivadent, Amherst, NY
[2]available from Vident, Germany
[3]available from Vident, Germany
[4]Leucite-reinforced ceramics and metals can be used together, since each can have a CTE of approximately 15
[5]Depends on leucite content and heat history.

In some embodiments, it can be important to match the coefficient of thermal expansion (CTE) of several or all of the components of the dental blank assembly 100. Otherwise, in some cases, the blank 102, the support 104 and/or the bonding composition 108 will not be bonded correctly during firing which might lead to failure of the dental blank assembly 100. In some embodiments, glass itself (e.g., including some of the formulations listed above) may match that of zirconia. In some embodiments, for example, when the support 104 comprises a metal, which tends to have a higher CTE, a crystalline material (e.g., leucite) may need to be added to the glass forming the blank 102 or bonding composition 108. Adding leucite to glass can raise the CTE of the glass, and can also improve the mechanical strength of the glass, but crystal materials other than leucite can also be used. The amount of leucite (or other crystal phase) to be added to the glass can depend on the material makeup of the support 104 to which the blank 102 (and/or bonding composition 108) will be coupled, because different metals and alloys have different CTEs. Alumina has a lower CTE compared to zirconia so the glass can be adapted in its composition to reach this lower CTE (e.g. Vita VM7 (VM9 can be used for zirconia, for example), Vita Zahnfabrik, Germany or Vident, USA). Table 2 lists exemplary pairings of support materials, blank materials, and bonding compositions of the present disclosure. The bonding compositions 108 are shown by way of example only; however, it should be understood that in some embodiments, a bonding composition 108 is not necessary, because the blank 102 and support 104 can be direct bonded or fused together without a bonding composition 108. Table 2 is only intended to be illustrative and not limiting:

TABLE 2

Exemplary pairings of blank materials, support materials and bonding compositions

| Support materials | Blank materials | Bonding compositions (if employed) |
|---|---|---|
| Zirconia[1] | Lithium disilicate[2] | Feldspathic porcelain[3] |
| Zirconia[1] | Feldspathic porcelain[4] | Feldspathic porcelain[5] |
| Zirconia[1] | Glass (e.g., SiO$_2$ with Al$_2$O$_3$, K$_2$O, Na$_2$O, etc.) | Glass solder (e.g., SiO$_2$ with Al$_2$O$_3$, K$_2$O, Na$_2$O, etc.) |
| Alumina[6] | Glass (e.g., SiO$_2$ with Al$_2$O$_3$, K$_2$O, Na$_2$O, etc.); or Glass ceramic[7] | Glass (e.g., SiO$_2$ with Al$_2$O$_3$, K$_2$O, Na$_2$O, etc.); or Glass ceramic[7] |
| Alumina[6] | Alumina[6] | Glass ceramic[7] |
| High Melting Temperature Dental Metal Alloy[8] | Leucite-reinforced glass-ceramic[9] | Feldspathic porcelain[10] |
| Metal | glass ceramic: glass fraction (e.g., SiO$_2$ with Al$_2$O$_3$, K$_2$O, Na$_2$O, etc.) and crystalline fraction (e.g. leucite)[11] | glass ceramic: glass fraction (e.g., SiO$_2$ with Al$_2$O$_3$, K$_2$O, Na$_2$O, etc.) and crystalline fraction (e.g. leucite) |

[1]e.g., from 3M ESPE, Seefeld, Germany
[2]e.g., E MAX CAD, available from Ivoclar Vivadent, Amherst, NY
[3]e.g., LAVA ™ Ceram Shoulder Porcelain, available from 3M ESPE
[4]e.g., VITA Mk II, available from Vita Zahnfabrik, Germany or Vident, USA
[5]e.g., VITA VM9, available from Vita Zahnfabrik, Germany or Vident, USA
[6]e.g., VITA alumina, available from Vita Zahnfabrik, Germany or Vident, USA
[7]e.g., VITA VM7, available from Vita Zahnfabrik, Germany or Vident, USA
[8]e.g., Begostar Wirobond LFC, available from Bego USA, Lincoln, RI
[9]e.g., EMPRESS CAD, available from Ivoclar Vivadent
[10]The CTE of feldspathic porcelains can be controlled/dictated by the leucite content, such that the CTE can be increased by increasing the leucite content; leucite content can be a result of heat history; one example is Finesse Porcelain, available from Dentsply, York, PA
[11]e.g., VITA VM13, which has a CTE of ~13, available from Vita Zahnfabrik, Germany or Vident, USA In some embodiments, matching CTEs means that the CTE of any of the components of the dental blank assembly 100 differ by no more than 2.0, in some embodiments, by no more than 1.5, in some embodiments, by no more than 1.0, and in some embodiments, by no more than 0.5. For example, in some embodiments, the CTE of the blank 102 differs from the support 104 and the bonding composition 108 (if employed), and vice versa, by no more than 2.0, 1.5, 1.0, or 0.5. For example, in some embodiments, the blank 102 can have a first CTE, the support 104 can have a second CTE, and the bonding composition, if employed, can have a third CTE, and the first, second, and third CTEs each differ from the other CTEs by no more than 2.0, 1.5, 1.0, or 0.5.

Figure 3:
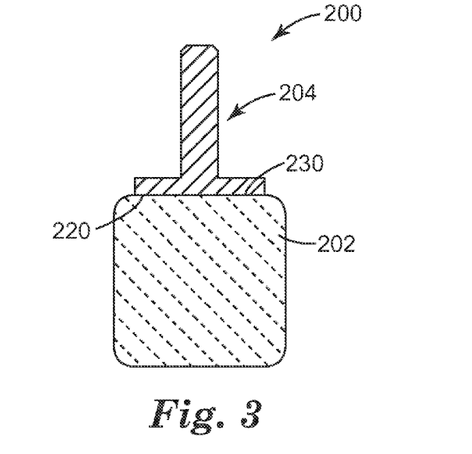
FIG. 3 is a side cross-sectional view of a dental blank assembly according to another embodiment of the present disclosure.

FIG. 3 illustrates another dental blank assembly 200 according to the present disclosure, wherein like numerals represent like elements. The dental blank assembly 200 shares many of the same elements and features described above with reference to the illustrated embodiment of FIGS. 1 and 2. Accordingly, elements and features corresponding to elements and features in the illustrated embodiment of FIG. 3 are provided with the same reference numerals in the 200 series. Reference is made to the description above accompanying FIGS. 1 and 2 for a more complete description of the features and elements (and alternatives to such features and elements) of the embodiment illustrated in FIG. 3.

A shown in FIG. 3, the dental blank assembly 200 includes a blank 202 directly coupled to a support 204. FIG. 3 shows a cross-section through the dental blank assembly 200 in which it is clear that the blank 202 and the support 204 are directly bonded together without the use of a bonding composition. For example, the support 204 is illustrated as having a bonding surface 220 that is directly bonded to a bonding surface 230 of the blank 202. Thus, FIG. 3 illustrates an example of a dental blank assembly according to the present disclosure wherein the means for coupling includes direct bonding of the blank 202 and the support 204. The various materials described above with reference to FIGS. 1 and 2 for the blank 102 and the support 104 can also be used for the blank 202 and the support 204 of the dental blank assembly 200.

In some embodiments, the dental blank assembly 200 can be formed using wax-investment molding processes. In such processes, the support 204 can be formed by first creating a wax design or pattern of the desired three-dimensional support shape, for example, via milling and/or rapid prototyping. Such a support shape can be designed to fit a known dental milling system, for example, using CAD/CAM software. In some embodiments, the design can include various mechanical inter-engaging structures, such that the resulting blank 202 and support 204 are also mechanically inter-engaged, such as the embodiment shown in FIGS. 4 and 5 and described below. Other acceptable mechanical interlock designs are described in U.S. Pat. No. 6,669,875, which is incorporated herein by reference, and could further include ribs or other roughening textures to increase the inter-engagement or interlock between the blank and support.

The wax replica of the desired three-dimensional support shape can then be invested in a casting investment material, such as a dental casting investment (e.g., Microstar HS Investment (Jensen Dental, New Haven, Conn.)). After the investment has set, the wax replica can be burned out, and the investment can be loaded with the desired support material (e.g., a metal alloy). The support can then be allowed to cool before breaking out and devesting, thus producing the support 204. In some embodiments, the bonding surface 220 of the support 204 can be further processed (e.g., sandblasted or otherwise textured) to increase adhesion with the bonding surface 230 of the blank 202.

A wax replica of the desired three-dimensional shape of the blank 202 can then be provided, for example, by milling, molding, or rapid-prototyping, and can be created directly on the bonding surface 220 of the support 204 to form an intermediate assembly. The intermediate assembly can then be invested in an appropriate investment material, such as the Microstar HS Investment. The wax replica of the blank 202 can then be burned out, and the desired blank material can be loaded into the investment cast. In some embodiments, the desired blank material can be pressed into the cast with a plunger, which can be pre-heated. Such pressing can be done in a pressing oven, for example.

Other details of an exemplary direct bonding process for forming the dental blank assembly 200 are described in Prophetic Example 3.

Figure 4:
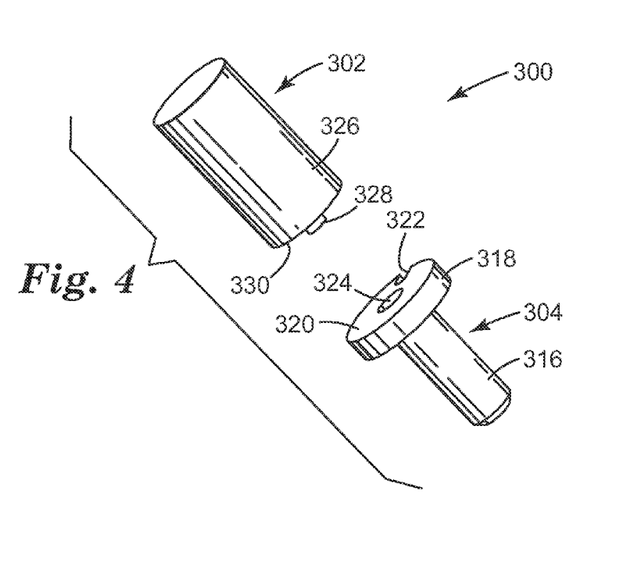
FIG. 4 is an exploded perspective view of a dental blank assembly.
Figure 5:
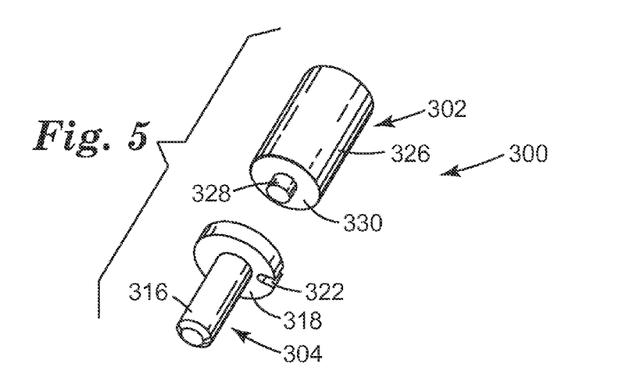
FIG. 5 is an exploded perspective view of the dental blank assembly of FIG. 4, shown in a different orientation.

FIGS. 4 and 5 illustrate another dental blank assembly 300 according to the present disclosure, wherein like numerals represent like elements. The dental blank assembly 300 shares many of the same elements and features described above with reference to the illustrated embodiment of FIGS. 1-3. Accordingly, elements and features corresponding to elements and features in the illustrated embodiment of FIGS. 4 and 5 are provided with the same reference numerals in the 300 series. Reference is made to the description above accompanying FIGS. 1-3 for a more complete description of the features and elements (and alternatives to such features and elements) of the embodiment illustrated in FIGS. 4 and 5.

As shown in FIGS. 4 and 5, the dental blank assembly 300 includes a blank 302 and a support 304 adapted to be coupled together at least partially by a mechanical inter-engagement or interlock. In addition, the blank 302 and the support 304 can be directly bonded, such as described above with respect to the dental blank assembly 200 of FIG. 3, and/or bonded with a bonding composition, such as described above with respect to the dental blank assembly 100 of FIGS. 1 and 2, and further described below.

As shown in FIGS. 4 and 5, the support 304 can include a shaft 316 having a longitudinal axis, which can include all the features described above with respect to the shaft 116 of FIGS. 1 and 2. Similarly, the support 304 can include a flange 318, a bonding surface 320, and a notch 322, each of which can include all the features described above with respect to the flange 118, the bonding surface 120, and the notch 122 of FIGS. 1 and 2.

As part of the mechanical inter-engagement, the support 304 also includes a recess 324 that is located in the flange 318, and/or is formed in the bonding surface 320 of the support 304. In the illustrated embodiment, the recess 324 has an overall generally cylindrical shape with a central axis that is collinear with the central axis of the flange 318 and the central axis of the shaft 316. As a consequence, the recess 324 is located in this embodiment in the center of the bonding surface 320. The inner end of the recess 324 has a generally dome-shaped configuration.

However, the recess 324 may alternatively have other shapes and be located in offset relation to the central axis of the flange 318. For example, the recess 324 may have a square, rectangular, oval or other shape in reference planes perpendicular to the central axis of the flange 318. Optionally, the recess 324 may have a length sufficient to extend into the adjacent end portion of the shaft 316.

As shown in FIGS. 4 and 5, the blank 302 includes a main body 326 as well as a projection 328 that is connected to the main body 326. In some embodiments, the body 326 and the projection 328 can be integrally formed together and form part of a single, unitary body; however, this need not be the case. For example, in some embodiments, the projection 328 can be coupled to the blank 302 using a bonding composition according to the present disclosure. In the embodiment shown in FIGS. 4 and 5, the body 326 has an overall cylindrical shape, although other shapes are also possible. In addition, the projection 328 is shaped and dimensioned to be received in the recess 324 of the support 304, but the projection 328 and the recess 324 can have other shapes, as long as their respective shapes accommodate one another and provide for a mechanical inter-engagement.

In some embodiments, the blank 302 may have a shape in reference planes perpendicular to its central axis that is rectangular, square, hexagonal or other types of polygons or non-polygons including oval. In some embodiments, as shown in FIGS. 4 and 5, the central axis of the body 326 is collinear with the central axis of the projection 328. The body 326 as shown has a cross-sectional dimension (e.g., diameter) that is smaller than the cross-sectional dimension (e.g., diameter) of the flange 318 of the support 304, but as another option, could have a cross-sectional dimension or overall shape that is larger than the cross-sectional dimension or overall shape of the support 304 or a portion thereof, such as the flange 318.

In some embodiments, the projection 328 can have a cross-sectional configuration in reference planes perpendicular to its central axis that is closely complementary to the cross-sectional configuration of the recess 324. As a consequence, the projection 328 can matingly fit within the recess 324 when the support 304 and the blank 302 are assembled together. In some embodiments, the central axis of the body 326 and the projection 328 are collinear with the central axis of the flange 318 and the shaft 316 when the support 304 and the blank 302 are assembled, as shown in FIGS. 4 and 5.

In some embodiments, the recess 324 can have a length in directions along its central axis that is somewhat longer than the length of the projection 328. As a consequence, when the support 304 and the blank 302 are coupled together, the bonding surface 320 of the support 304 can tightly and intimately contact an annular flat bonding surface 330 of the blank 302 that surrounds the projection 328. The extra depth provided in the recess 324 can ensure that the bonding surfaces 320 and 330 will fully meet even in instances where the length of the projection 328 is somewhat larger than expected.

In some embodiments, the projection 328 and the recess 324 can be configured to provide an interference fit. For example, the cross-sectional configuration of the projection 328 can be slightly larger than the cross-sectional configuration of the recess 324 in reference planes perpendicular to the central axis of the assembly 300 so that an interference fit is presented. In that instance, the projection 328 can be forced under pressure into the recess 324 in order to establish a secure press-fit relationship when the support 304 and the blank 302 are coupled together.

As mentioned above, in some embodiments, a bonding composition can be provided to enhance the bond between the support 304 and the blank 302. In such embodiments, the bonding composition can extend between the entire area of the bonding surfaces 320 and 330, and/or along the interfacing surfaces of the projection 328 and the recess 324 that are in contact with each other.

The dental blank assembly 300 includes the projection 328 on the blank 302 and the recess 324 in the support 304 by way of example only; however, it should be understood that the blank 302 can alternatively, or additionally, include a recess, and the support 304 can alternatively, or additionally, include a mating projection. That is, one of the blank 302 and the support 304 can include the projection 328, and the other of the blank 302 and the support 304 can include the recess 324 that is dimensioned to receive the projection 328. As a result, the mechanical inter-engagement shown in FIGS. 4 and 5 is shown by way of example only, but additional inter-engaging structures can be employed to provide a mechanical means for coupling the blank 302 and the support 304.

Dental blank assemblies of the present disclosure employing such a mechanical inter-engaging structure can have an enhanced resistance to fracture during downstream machining processes, and can be particularly suited to safely resist forces exerted by a machining tool (e.g., a milling tool) in lateral directions so that a dental appliance can be machined to completion without unintentional and undesirable detachment of the support 304 from the blank 302.

The mechanical inter-engaging structures shown in FIGS. 4 and 5, or other suitable and similar inter-engaging structures, can also be employed in the dental blank assemblies of FIGS. 1-3, and need not only be employed in dental blank assemblies having the shapes and/or geometries of the dental blank assembly 300 of FIGS. 4 and 5.

Examples of methods for making a blank and a support having interlocking or inter-engaging features or structures are described in U.S. Pat. Nos. 6,482,284 and 6,669,875, which are incorporated herein by reference.

The dental blank assemblies 100, 200 and 300 are shown to illustrate various features and elements of the present disclosure; however, it should be understood that various features and elements of the dental blank assemblies 100, 200 and 300 can be combined without departing from the spirit and scope of the present disclosure.

The following is a description of various embodiments of the present disclosure.

EMBODIMENTS

Embodiment 1 is a fireable dental blank assembly, the assembly comprising:
 a blank adapted to be machined to form at least a portion of dental appliance, the blank being formed of at least one of a glass, a glass-ceramic, a porcelain, and a ceramic;
 a support coupled to the blank to facilitate downstream machining processes of the blank, the support being formed of at least one of a high melting point metal and a ceramic, wherein the blank and the support are separately formed; and
 a bonding composition positioned between the blank and the support to couple the blank and the support, the bonding composition having a softening temperature that is lower than a softening temperature of the blank and that is lower than a softening temperature of the support;
 wherein a high melting point metal is a metal or metal alloy that has a melting point that is higher than a firing temperature of the blank, and that is higher than the softening temperature of the bonding composition;
 wherein the blank has a first coefficient of thermal expansion (CTE), wherein the support has a second CTE, and wherein the bonding composition has a third CTE, wherein the first CTE and the second CTE differ by no more than 2.0, wherein the second CTE and the third CTE differ by no more than 2.0, and wherein the first CTE and the third CTE differ by no more than 2.0; and
 wherein the assembly is configured to withstand temperatures necessary to fire at least a portion of the assembly in a downstream firing process.

Embodiment 2 is the assembly of embodiment 1, wherein the temperature at which the bonding composition is softened to couple the blank and the support is higher than a temperature used in a downstream firing process.

Embodiment 3 is the assembly of embodiment 1 or 2, wherein the blank is directly coupled to the support with the bonding composition.

Embodiment 4 is the assembly of any of embodiments 1-3, wherein the first CTE, the second CTE, and the third CTE differ from one another by no more than 1.0.

Embodiment 5 is a fireable dental blank assembly, the assembly comprising:
 a blank adapted to be machined to form a dental appliance, the blank being formed of at least one of a glass, a glass-ceramic, a porcelain, and a ceramic;
 a support coupled to the blank to facilitate downstream machining processes, the support being formed of at least one of a high melting point metal and a ceramic, wherein the blank and the support are separately formed; and
 means for coupling the blank and the support, wherein the means for coupling is adapted to withstand temperatures necessary to fire at least a portion of the assembly;
 wherein a high melting point metal is a metal or metal alloy that has a melting point that is higher than a firing temperature of the blank, and that is higher than a softening temperature of other components of the assembly;
 wherein each component of the assembly has a coefficient of thermal expansion (CTE) that differs from a CTE of other components of the assembly by no more than 2.0; and
 wherein the assembly is configured to withstand temperatures necessary to fire at least a portion of the assembly in a downstream firing process.

Embodiment 6 is the assembly of embodiment 5, wherein the means for coupling includes at least one of a mechanical inter-engagement, a direct bond, a bonding composition, and a combination thereof.

Embodiment 7 is the assembly of embodiment 5, wherein the means for coupling the blank and the support include a mechanical inter-engagement.

Embodiment 8 is the assembly of embodiment 5 or 7, wherein the means for coupling the blank and the support include a direct bond, such that the support and the blank are directly bonded together.

Embodiment 9 is the assembly of any of embodiments 5-8, wherein each component of the assembly has a CTE that differs from a CTE of other components of the assembly by no more than 1.0.

Embodiment 10 is the assembly of any of embodiments 1-9, wherein the assembly is configured to mechanically withstand a downstream machining process.

Embodiment 11 is the assembly of embodiment 10, wherein the downstream machining process comprises milling.

Embodiment 12 is the assembly of any of embodiments 1-11, wherein the support is formed of a high melting point metal or metal alloy and includes a melting point of at least 1100° C.

Embodiment 13 is the assembly of any of embodiments 1-12, wherein the support includes a softening point of at least 600° C.

Embodiment 14 is the assembly of any of embodiments 1-13, wherein the blank includes at least one of lithium disilicate, feldspathic porcelain, leucite-reinforced glass-ceramic, and a combination thereof.

Embodiment 15 is the assembly of any of embodiments 1-14, wherein the support includes at least one of cobalt-chromium, nickel chromium, zirconia, and a combination thereof.

Embodiment 16 is the assembly of any of embodiments 1-15, wherein the support comprises fully sintered zirconia.

Embodiment 17 is the assembly of any of embodiments 1-16, wherein the support is shaped and configured for use in a dental mill.

Embodiment 18 is the assembly of any of embodiments 1-17, wherein the bonding composition includes at least one of feldspathic porcelain, glass solder, and a combination thereof.

Embodiment 19 is the assembly of any of embodiments 1-18, wherein the downstream firing process includes temperatures no greater than 950° C.

Electromagnetic 20 is the assembly of any of embodiments 1-19, wherein the blank and the support are formed of different materials.

The following working and prophetic examples are intended to be illustrative of the present disclosure and not limiting.

EXAMPLES

Working Example 1

Zirconia Support—Lithium Disilicate Blank—Lava™ Ceram Shoulder Porcelain Bonding Composition Support Fabrication A commercially available metal support designed to fit into a Cerec 3 milling unit (Sirona, Germany) was scanned with a LAVA™ ST Scanner (3M ESPE, Seefeld, Germany) to obtain a digital surface representation of the metal support. The digital surface representation was used to mill a LAVA™ Zirconia mill blank (3M ESPE) into the same shape as the metal support, factoring in a shrinkage parameter such that the zirconia support was the proper size after sintering. The milled zirconia was fully sintered per manufacturer's instructions in a LAVA™ Furnace 200 (3M ESPE), thus producing a fully sintered zirconia support.

Coupling of the Mill Blank and the Support

A lithium disilicate (e.max, Ivoclar Vivadent, Amherst, N.Y.) mill blank not having a support was placed on a surface and an aqueous slurry of LAVA™ Ceram Shoulder Porcelain (3M ESPE), which served as a bonding composition, was liberally painted on both the mill blank and the sintered zirconia support. The support was then pressed onto the blank using finger pressure and the assembly was carefully placed into a Vita Vacuumat 4000t furnace (Vident (or Vita Zahnfabrik), Bad Sackingen, Germany) and fired with the following temperature profile: 450° C. for 6 min., ramped at 45° C./min. to 850° C. and held at 850° C. for 2 min. The vacuum was on during the heating and released when the temperature reached 850° C. The assembly was cooled, thus producing a dental blank assembly comprising a mill blank coupled to a support with a bonding composition.

Machining a Restoration

The dental blank assembly was placed into a Cerec 3 milling unit and a standard anterior crown form (central incisor) was milled from the blank. Throughout the process, the mill blank remained firmly attached to the support. The crown remained attached by a sprue.

Firing the Restoration

The dental blank assembly having the milled crown was placed into a Vita Vacuumat 4000t furnace and fired with the following temperature profile: 450° C. for 6 min., ramped at 45° C./min. to 850° C. and held at 850° C. for 1 min. The vacuum was on during the heating and released when the temperature reached 850° C. The dental blank assembly was cooled, thus producing a fired, milled restoration still attached to the support by a sprue. Throughout the firing and cooling process, the blank remained firmly attached to the support.

Working Example 2

Zirconia Support—Feldspathic Ceramic Blank—Feldspathic Porcelain Bonding Composition Support Fabrication A fully sintered zirconia support was made as described in Example 1.

Coupling the Mill Blank and the Support

A feldspathic porcelain (Vita Mk II, Vident) mill blank not having a support was placed on a surface and an aqueous slurry of Vita VM9 porcelain (feldspathic ceramic), which served as a bonding composition, was liberally painted on both the mill blank and the sintered zirconia support. The support was then pressed onto the blank using finger pressure and the assembly was carefully placed into a furnace (Vita Vacumat 4000T, Vident) and fired with the following temperature profile: 450° C. for 6 min., ramped at 30° C./min. to 910° C. and held at 910° C. for 2 min. The vacuum was on during the heating and released when the temperature reached 910° C. The fired assembly was cooled, thus producing a dental blank assembly comprising a mill blank coupled to a support with a bonding composition.

Milling a Restoration

The dental blank assembly was placed into a Cerec 3 milling unit and a standard anterior crown form (central incisor) was milled from the blank. Throughout the process, the mill blank remained firmly attached to the support. The crown remained attached by a sprue.

Firing the Restoration

The dental blank assembly having the milled crown was placed into a Vita Vacuumat 4000t furnace and fired with the following temperature profile: 450° C. for 2 min., then ramped at 45° C./min. to a final temperature of 900° C. The vacuum was on during the heating and released when the temperature reached 900° C. The dental blank assembly was cooled, thus producing a fired, milled restoration still attached to the support by a sprue. Throughout the firing and cooling process, the blank remained firmly attached to the support.

Prophetic Example 3

Metal Alloy Support—Leucite-Reinforced Glass-Ceramic Blank, Direct Bonding, and Mechanical Inter-Engagement Support Fabrication A three-dimensional support shape (e.g., a mandrel) is designed to fit a known dental milling system using CAD/CAM software. A mechanical inter-engagement such as that shown in FIGS. 4 and 5 is included in the design. Other acceptable mechanical interlock designs are described in U.S. Pat. No. 6,669,875 and could further include ribs or other roughening textures to increase the inter-engagement or interlock between the blank and support. A wax replica of the design is created by a milling or rapid prototyping machine. The wax replica is then invested in dental casting investment such as Microstar HS Investment (Jensen Dental, New Haven, Conn.). Once the investment has set, the wax replica is burned out in an oven for 45 min. at 700° C., the alloy being pre-heated at the same time. A dental metal alloy such as Wirobond LFC(CTE 15.9, Bego USA, Lincoln, R.I.) is loaded into the investment. The alloy is cast at 1300° C. and allowed to cool on the benchtop before breaking out and devesting, thus producing a metal support. It may be advantageous to sandblast the bonding surface of the resulting support to increase adhesion.

Direct Bonding of the Blank and the Support

A typical parallelipipedal mill blank shape and orientation is created in wax on the metal support and the formed assembly is invested in a material such as Microstar HS Investment. The wax is burned out at 850° C. An Empress Esthetic ingot (leucite-reinforced glass-ceramic made for pressing) and Allox plunger (both from Ivoclar, Liechtenstein) are pre-heated, e.g., at the same time as the wax is burned out. The pressing is done in a pressing oven such as the Ivoclar EP500 with a program of 700° C. base temp, 60° C. per min. ramp under vacuum to a 1075° C. hold for 20 min. under 5 bar of pressure.

Final Step in Forming the Dental Blank Assembly

The entire assembly consisting of the mechanically inter-engaged blank and support is broken out to reveal the finished dental blank assembly.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A fireable dental blank assembly, the assembly comprising:
 a blank adapted to be machined to form at least a portion of dental appliance, the blank being formed of at least one of a glass, a glass-ceramic, a porcelain, and a ceramic;
 a support coupled to the blank to facilitate downstream machining processes of the blank, the support being formed of at least one of a high melting point metal and a ceramic, the support having a softening temperature that is greater than a firing temperature for firing the assembly, wherein the firing temperature is at least about 600° C., wherein the blank and the support are separately formed; and
 a bonding composition positioned between the blank and the support to couple the blank and the support, the bonding composition comprising at least one of a glass, a glass ceramic, feldspathic porcelain, glass solder, and a combination thereof, the bonding composition having a bonding temperature that is greater than the firing temperature;
 wherein a high melting point metal is a metal or metal alloy that has a melting point that is higher than the firing temperature, and that is higher than the bonding temperature of the bonding composition;
 wherein the blank has a first coefficient of thermal expansion (CTE), wherein the support has a second CTE, and wherein the bonding composition has a third CTE, wherein the first CTE and the second CTE differ by no more than 2.0, wherein the second CTE and the third CTE differ by no more than 2.0, and wherein the first CTE and the third CTE differ by no more than 2.0.

2. The assembly of claim 1, wherein the blank is directly coupled to the support with the bonding composition.

3. The assembly of claim 1, wherein the first CTE, the second CTE, and the third CTE differ from one another by no more than 1.0.

4. The assembly of claim 1, wherein the support is formed of a high melting point metal or metal alloy and includes a melting point of at least 1100° C.

5. The assembly of claim 1, wherein the support includes a softening point of at least 600° C.

6. The assembly of claim 1, wherein the blank includes at least one of lithium disilicate, feldspathic porcelain, leucite-reinforced glass-ceramic, and a combination thereof.

7. The assembly of claim 1, wherein the support includes at least one of cobalt-chromium, nickel chromium, zirconia, and a combination thereof.

8. The assembly of claim 1, wherein the support comprises fully sintered zirconia.

9. The assembly of claim 1, wherein the support is shaped and configured for use in a dental mill.

10. The assembly of claim 1, wherein the firing temperature is no greater than 950° C.

11. The assembly of claim 1, wherein the blank and the support are formed of different materials.

12. The assembly of claim 1, wherein the bonding composition includes less than about 7 wt % of organic components.

13. The assembly of claim 1, further comprising a mechanical inter-engagement between the blank and the support.

14. A fireable dental blank assembly, the assembly comprising:
a blank adapted to be machined to form a dental appliance, the blank being formed of at least one of a glass, a glass-ceramic, a porcelain, and a ceramic;
a support coupled to the blank to facilitate downstream machining processes, the support being formed of at least one of a high melting point metal and a ceramic, the support having a softening temperature that is greater than a firing temperature for firing the assembly, wherein the firing temperature is at least about 600° C., wherein the blank and the support are separately formed; and
means for coupling the blank and the support;
wherein a high melting point metal is a metal or metal alloy that has a melting point that is higher than the firing temperature;
wherein each component of the assembly has a coefficient of thermal expansion (CTE) that differs from a CTE of other components of the assembly by no more than 2.0.

15. The assembly of claim 14, wherein the means for coupling includes at least one of a direct bond, a bonding composition, and a combination thereof.

16. The assembly of claim 15, wherein the means for coupling the blank and the support further includes a mechanical inter-engagement.

17. The assembly of claim 14, wherein the means for coupling the blank and the support include a direct bond, such that the support and the blank are directly bonded together.

18. The assembly of claim 14, wherein each component of the assembly has a CTE that differs from a CTE of other components of the assembly by no more than 1.

19. A fineable dental blank assembly, the assembly comprising:
a blank adapted to be machined to form at least a portion of dental appliance, the blank being formed of at least one of a glass, a glass-ceramic, a porcelain, and a ceramic;
a support coupled to the blank to facilitate downstream machining processes of the blank, the support being formed of at least one of a high melting point metal and a ceramic, the support having a softening temperature that is greater than a firing temperature for firing the assembly, wherein the firing temperature is at least about 600° C., wherein the blank and the support are separately formed; and
a bonding composition positioned between the blank and the support to couple the blank and the support, the bonding composition comprising at least one of a glass, a glass ceramic, feldspathic porcelain, glass solder, and a combination thereof, the bonding composition having a bonding temperature that is greater than the firing temperature;
wherein a high melting point metal is a metal or metal alloy that has a melting point that is higher than the firing temperature, and that is higher than the bonding temperature of the bonding composition.

* * * * *